US005658884A

United States Patent [19]
Hodgen

[11] Patent Number: 5,658,884
[45] Date of Patent: Aug. 19, 1997

[54] ESTABLISHMENT OF TONIC OVARIAN ESTROGEN SECRETION FOR EXTENDED THERAPEUTIC REGIMENS

[75] Inventor: Gary D. Hodgen, Norfolk, Va.

[73] Assignees: The Medical College of Hampton Roads, Norfolk, Va.; Ortho Pharmaceutical Corporation, Raritan, N.J.

[21] Appl. No.: 467,860

[22] Filed: Jun. 6, 1995

Related U.S. Application Data

[63] Continuation-in-part of Ser. No. 279,593, Jul. 22, 1994, abandoned.

[51] Int. Cl.$^6$ .............................. C07K 7/00; A61K 38/09
[52] U.S. Cl. ........................... 514/12; 514/21; 424/9.1
[58] Field of Search ................................. 514/12, 21, 9.1

[56] References Cited

U.S. PATENT DOCUMENTS 5,340,584  8/1994  Spicer et al. ............................ 424/426

*Primary Examiner*—Cecilia J. Tsang
*Assistant Examiner*—P. Lynn Touzeau
*Attorney, Agent, or Firm*—Ostrolenk, Faber, Gerb & Soffen, LLP

[57] ABSTRACT

A regimen for the therapeutic management of a gonadal-steroid dependent condition in a mammal constitutes reducing the estrogen supply thereof by means of administration of a GnRH antagonist in an amount effective to inhibit proliferation of endometrial tissue without substantially stopping the production of endogenous estrogen. A method of determining whether the reduced estrogen supply in an individual is such that the concentration of estradiol has been suppressed to an optimized level appropriate to the therapeutic management of the gonadal-steroid dependent condition such as endometriosis in that individual by the administration of a GnRH antagonist at a given dosage level involves titering the dosage, e.g., by conducting a progesterone challenge test and optimal regimen doses of a GnRH antagonist.

30 Claims, No Drawings

ESTABLISHMENT OF TONIC OVARIAN ESTROGEN SECRETION FOR EXTENDED THERAPEUTIC REGIMENS

This is a continuation-in-part of application Ser. No. 08/279,593, filed Jul. 22, 1994, now abandoned.

BACKGROUND OF THE INVENTION

Endometriosis is the ectopic presence of endometrial type glands and stroma in sites which are outside of the uterus. This ectopic occurrence of endometrial tissue frequently forms cysts containing altered blood. The condition results in debilitating pain for millions of women worldwide and particularly occurs in conjunction with the monthly proliferation of endometrial tissue. It is frequently a lifelong condition, sometimes associated with infertility.

Endometriosis can be treated by a variety of medical therapies but none of these are sufficiently safe or effective for a long term treatment beyond six months or more. Perhaps the oldest therapy with a demonstrable effect is the administration of progestin either by injection, orally or in combination with oral contraceptives. However, long term administration of progestins have been associated with a number of undesirable side effects, as well as questionable efficacy, and has not received regulatory approval in the U.S.

A synthetic steroid derived from ethisterone, namely 17-α-pregna-2,4-dien-20-yno[2,3-d]-isoxazol-17-ol, also known as danazol and marketed under the trademark Danocrine has been shown an effective medication for the treatment of endometriosis producing a hypoestrogenic milieu. Unfortunately, this drug also has many androgenic side effects. In addition to the vasomotor flush of estrogen deprivation, it causes weight gain, muscle cramps, breast atrophy, hot flashes, mood swings, oily skin, depression, edema, acne, fatigue, hirsutism, alterations in the libido, headache, rash and a deepening of the voice.

One of the most effective treatments of endometriosis is the administration of a gonadotropin releasing hormone (GnRH) agonist to suppress pituitary gonadotropin secretion and thereby induce a state of reversible pseudomenopause, i.e. administration of a down regulating dose. Although individual response varies, the endometriotic lesions associated with endometriosis usually quickly regress and decrease in size within only three months of initiation of therapy. On withdrawal of the treatment, pain often returns and the endometriosis reappears within a few months after the return of normal menstrual cycles. The drug can also be used to treat fibroid tumors (leiomyomata).

The main drawback of this therapy long-term is a series of side effects stemming from protracted severe hypoestrogenism or the pseudomenopausal state induced by severe estrogen deprivation, namely hot flashes, bone loss and loss of cardiovascular protection by estrogen. While individual response again varies, the bone loss generally begins to be measurable after about 3 months of therapy and sometimes becomes highly significant after about 6 months of therapy in the most vulnerable patients. This bone loss side effect is totally unacceptable from a risk-benefit point of view—the life expectancy after a post-menopausal woman experiences a break of the hip bones due to osteoporosis is only about 3.2 years. Because of this side effect, the U.S. Food & Drug Administration contraindicates any administration of a gonadotropin releasing hormone analog after six months of total administration has elapsed. In other words, the drug cannot be readministered after a resting period according to FDA labelling requirement.

Thus, a matter of concern in GnRH agonist therapy is based on the recognition that prolonged hypoestrogenic status among women of reproductive age can result in cumulative estrogen-depletion side-effects, especially accelerated bone density loss, potentially cumulating in a heightened risk of osteoporosis and bone fractures. Patients receiving a "down regulating" dose of GnRH agonist have grossly deficient estrogen levels rivaling post-menopausal conditions. These concerns have motivated clinical studies of "add back" regimens based on an "estrogen threshold hypothesis" in which patients presented with clinically significant uterine fibroids have used GnRH agonist medications in combination with low dose estrogen-progestin hormone replacement therapy, the latter being similar to the familiar post-menopausal treatment regimes. The object has been to achieve a sufficient reduction in endogenous ovarian estrogen secretion by means of the agonist together with a low dose exogenous estrogen-progestin supplement so that the clinical benefits will not be forfeited due to the "add back" hormone replacement therapy regimen.

The scientific literature also describes the potential use of gonadotropin releasing hormone antagonists as efficacious in the clinical management of endometriosis and uterine leiomyomata. For example, Gordon et al., Suppression of Ovarian Estradiol Secretion by a Single Injection of Antide in Monkeys Follicular Phase: Intermediate, Sustained and Reversible Actions, J. Clin. Endocrin. Metab., 73:1262 (1991), examined the effects of the GnRH antagonist antide and the authors concluded that the antagonist, when administered as a sufficient single dose, could induce immediate and sustained inhibition of the pituitary-ovarian axis. The hypoestrogenic milieu produced was sufficient to expect that management of patients would provide control of various gonadal-steroid dependent conditions, such as endometriosis and leiomyomata uteri, without the delay and potential consequences of the familiar flare and down-regulation response to initiations of GnRH agonist therapy. However, the authors also indicated that a formulation which would give a greater control of bioavailability and, in turn, less individualism of response was highly desirable.

The basis for the antagonist approach of the present invention derives from the recognition that unlike the agonist products, which act by complete inhibition through down regulation of the GnRH receptor system, the antagonist monopolizes the GnRH receptors by competitive occupancy thereby achieving differential degrees of inhibition that are dose dependent. Therefore, it is possible, with the appropriate dose of the GnRH antagonist, to maintain tonic ovarian estradiol secretion at a modest level which is sufficiently reduced to control the estrogen-dependent gynecological problems such as endometriosis but still high enough to avoid the long term sequelae of frank estrogen deficiency.

There is a need to provide a dose and/or regimen of GnRH antagonist which will provide an optimized level of estrogen serum concentration. As noted in the Gordon et al. article referred to above, the response to a particular GnRH antagonist varies from individual to individual. Therefore, the GnRH antagonist dosage must be adjusted in each individual in order to achieve the appropriate degree of estrogen secretion. Accordingly, there is also a need for a convenient method to determine whether an appropriate estrogen level has been established.

It will thus be appreciated that there are a number of therapeutic regimens in which it is desirable to maintain tonic ovarian estrogen secretion. Treatment of endometriosis and leiomyomata are examples. There is a level of agent which is appropriate to safe (i.e. avoidance of menopausal side effect such as bone density loss) and effective (i.e., treatment of the disease state) long-term therapeutic management of gonadal-steroid dependent conditions. The present invention provides that level and a way to establish it.

BRIEF DESCRIPTION OF THE DRAWINGS

FIG. 1 illustrates that residual ovarian estrogen secretion is GnRH antagonist doses-dependent and that the degree of inhibition stabilizes within 7 to 10 days of initiating treatment.

FIG. 2 illustrates that populations of menstruating primates can be titered to a desirable level of partial inhibition of ovarian estrogen secretion.

SUMMARY OF THE INVENTION

This invention broadly relates to the treatment of gonadal-steroid dependent conditions such as endometriosis, uterine leiomyomata, premenstrual syndrome and dysfunctional uterine bleeding. More particularly, the invention relates to the safe and effective treatment of these gonadal-steroid dependent conditions by administration of a regimen of a GnRH antagonist which is effective to substantially inhibit proliferation of endometrial tissue in a menstruating female but is ineffective to substantially stop production of estrogen, that is, ineffective to substantially induce a castrate level of endogeneous estrogen. Other preferred embodiments of the invention are directed to doses of GnRH antagonist which provide effective amounts to inhibit proliferation of endometrial tissue in a menstruating female but which amounts are ineffective to substantially stop production of endogenous estrogen. In particularly preferred embodiments of the invention, the regimen and doses provided permit sufficient production of endogenous estrogen to produce and maintain a serum estradiol concentration in the range of about 30 to 50 and preferably about 35 to 45 pg/ml.

This invention also provides a method of determining whether a hypoestrogenic milieu in an individual mammal is such that the concentration of estradiol has been suppressed to an optimized level appropriate to the therapeutic management of the gonadal-steroid dependent condition in that individual by administering a GnRH antagonist to the individual at a given dosage established by titering, e.g., by conducting a progesterone challenge test on that individual.

DETAILED DESCRIPTION OF THE INVENTION

In accordance with the present invention, a regimen or dose of GnRH antagonist is provided which is effective to inhibit proliferation of endometrial tissue in a menstruating female but is ineffective to substantially stop production of endogenous estrogen. While the amount of GnRH antagonist provided in the regimen and the dose may vary in accordance with particular subjects, the regimen and dose is generally adjusted to achieve a 24 hour serum estradiol in the range of about 30 to 50 and preferably about 35 to 45 pg/ml.

It has been suggested that lowering the serum estradiol level has the desired effect of inhibiting proliferation of endometrial tissue in a menstruating female. However, there is a coincident problem of possibly not providing enough estrogen to mitigate, avoid or protect against the menopausal-like symptoms associated with a castrate-like estrogen level. For instance, when the endogenous estrogen level falls below about 15 pg/ml, estrogen depletion side-effects occur. Avoiding these side-effects after endogenous estrogen depletion has only heretofore been accomplished by adding back estrogen, i.e. the so called "add-back therapy". It is only the present invention which provides treatment for gonadal-steroid dependent conditions while maintaining endogenous serum estradiol levels of at least about 30 pg/ml without relying on "add-back" of estrogen.

The clinical management of certain gynecological maladies that are estrogen dependent, such as endometriosis, is more complex than simple estrogen deprivation of the patient. In fact, inflicting severe hypoestrogenemia over a protracted interval not only causes patients to endure the discomfort of central estrogen deficiency symptoms, but risks accelerating bone density loss and enhancement of cardiovascular risk factors which are associated with protracted estrogen deprivation.

Optimal therapeutic conditions can permit long-term clinical management of these disorders, limit ovarian estrogen secretion to a level that is therapeutically beneficial (i.e. pelvic pain from ectopic endometrial lesions is markedly reduced or eliminated), while simultaneously, maintaining residual (basal) estrogen secretion from the ovaries above the castrate (menopausal-like) nadir, thereby insuring health benefits.

This approach is superior to estrogen-progestin add back therapy because the GnRH antagonist regimen is titered to individual needs which are revealed by both residual estrogen levels in blood and whether endometrial proliferation is sufficient to allow withdrawal bleeding after a brief course of progesterone therapy.

In summary, this technology allows a practical method wherein estrogen levels are low enough to achieve therapeutic benefits from reduced estrogen supplies, but high enough to minimize or avoid the consequences of long-term estrogen deprivation.

In considering determination of the appropriate dosage, it is important to recognize that simply measuring the estradiol secretion level may not provide sufficient information. It has now been recognized that not only is the estradiol secretion level variable from individual to individual in response to a given dose of GnRH antagonist but also the dosage of antagonist which is sufficient to cause the individual to manifest amenorrhea also varies from person to person. It has therefore been found that the dosage determination should be accomplished by titering the GnRH antagonist dosage, for example through the use of a progesterone challenge test.

Accordingly, pursuant to the invention, the management of a gonadal-steroid dependent condition is achieved by administering a GnRH antagonist to the individual and then titering the antagonist to a selected dose and/or regimen so that an optimal hypoestrogenic milieu can be achieved.

The gonadotropin releasing hormone is a small polypeptide produced in the hypothalamus and is sometimes termed gonadotropic releasing hormone, luteinizing hormone releasing hormone, GnRH or LHRH. In the present invention, those analogs or peptomimetics of this polypeptide which are antagonists are employed.

Examples of gonadotropin releasing hormone antagonist can be found, inter alia, in U.S. Pat. Nos. 4,409,208, 4,547,370, 4,565,804, 4,569,927 and 4,619,914, 5,198,533, and WO 89/01944, the disclosures of which are incorporated herein by reference. Examples of such antagonists include Azaline B, Antide (a decapeptide represented by the formula D-Ac-D-2-Nal$^1$-DpClPhe$^2$-D-3-Pal$^3$-Ser$^4$-NiLys$^5$-D-NicLys$^6$-Leu$^7$-ILys$^8$-Pro$^9$-D-Ala$^{10}$), [Ac-D4ClDPhe$^1$, D4ClDPhe², DTrp³, DArg⁶, DAla¹⁰] GnRH, [Ac-4ClDPhe², D₃Pal³, Arg⁵, D₂Nal⁶, DAla¹⁰] GnRH, [Ac-D2-Nal¹, 4ClDPhe², DTrp³, DArg⁶, DAla¹⁰] GnRH, [Ac-D₂Nal¹, 4FDPhe², DTrp³, DArg⁶] GnRH, [Ac-D2Nal¹, 4ClDPhe², DTrp³, DhArg(Et₂)⁶, DAla¹⁰] GnRH, and [Ac-Nal¹, DME4ClPhe², DPal³, Ser⁴, Tyr⁵, DArg⁶, Leu⁷, ILys⁸, Pro⁹, DAla¹⁰] GnRH.

The gonadotropin releasing hormone antagonists employed in the present invention can be administered in the form of pharmaceutically acceptable non-toxic salts or complexes. The salts include acid addition salts such as for instance hydrochloride, hydrobromide, sulfate, phosphate, nitrate, oxalate, fumarate, gluconate, tannate, maleate, acetate, benzoate, succinate, alginate, malate, ascorbate, tartrate and the like. The complexes can be with metals such as for example zinc, barium, calcium, magnesium, aluminum and the like.

Any known GnRH antagonist can be employed. The mode of administration heretofore employed for similar therapeutics, i.e. GnRH agonists, can also be employed in the practice of the present invention substituting the antagonist for the previously used agent. Thus, the route of administration can be any conventional route where the analog is active, for instance orally, intravenously, subcutaneously, intramuscularly, sublingually, percutaneously, rectally, intranasally or intravaginally. Similarly, the administration form can be a tablet, dragee, capsule, pill, nasal mist, aerosol and the like.

As a rule of thumb, the amount of initial gonadotropin releasing hormone antagonist administered is that sufficient to adjust the circulating estrogen to a value within a target zone of about 25–50 pg/ml. Depending on the particular antagonist employed, the initial dose is generally about 0.001 to 0.5 mg/kg per day when administered intramuscularly but such can be subject to wide variation depending on the mode of administration and the particular compound delivered. The administration can be periodic, such as on a weekly or monthly basis or a continuous basis such as daily. Daily administration is preferred because individuals are more likely to follow the treatment regimen and not to forget or overlook a period administration schedule. The use of a depot administration can be convenient and raise patient compliance.

Whether the amount of antagonist administered is sufficient to manage the gonadal-steroid dependent condition will be readily apparent simply by observing the external manifestations of the condition. For example, the absence of pain indicates that the dosage of GnRH antagonist has been sufficient to manage endometriosis. In order to determine whether the dosage is appropriate to optimize the tonic estradiol concentration, a progesterone challenge test is conducted. The test per se and manner in which such a test is conducted is well known. See, for example, Abbasi et al, "Predicting the Predisposition to Osteoporosis", JAMA, 255:1600 (1986) and Kletzky et al, "Clinical categorization of patients with secondary ammenorrhea using progesterone-induced uterine bleeding and measurement of serum gonadotropin levels", Am. J. Obstet. Gynecol., 121:695 (1975). In broad terms, a dosage of progesterone or a synthetic progestin is administered for a short period of time such as for instance 7 to 14 days and when the progestin is withdrawn, the presence or absence of consequent withdrawal bleeding is noted. The occurrence of withdrawal bleeding is an indication that the estradiol concentration remained sufficient to stimulate the endometrium and therefore, has not been sufficiently reduced. In this instance, the dosage of GnRH antagonist should be increased.

Conversely, the absence of withdrawal bleeding signifies that a state of amenorrhea has been achieved and that the estradiol level is either appropriate or too low. In the latter instance, the amount of GnRH antagonist can be decreased and the challenge test repeated. The cycle of antagonist administration and challenge test can be repeated until the appropriate concentration of antagonist to be administered has been determined.

The progesterone can be administered in any convenient pharmaceutical formulation. For example, such formulations may contain the progestin and a suitable carrier such as a solid dosage forms which includes tablets, capsules, cachets, pellets, pills, powders or granules; topical dosage forms which includes solutions, powders, fluid emulsions, fluid suspensions, semi-solids, ointments, pastes, creams, gels or jellies and foams; and parenteral dosage forms which includes solutions, suspensions, emulsions or dry powder comprising an effective amount of progesterone. It is known in the art that the active ingredient, the progestin, can be contained in such formulations in addition to pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and other means of augmenting the medicinal entity. The means and methods for administration are known in the art and an artisan can refer to various pharmacologic references for guidance. For example, "Modern Pharmaceutics", Banker & Rhodes, Marcel Dekker, Inc. 1979; "Goodman & Gilman's The Pharmaceutical Basis of Therapeutics", 6th Edition, MacMillan Publishing Co., New York 1980 can be consulted. Likewise, progestins (analogs) that mimic the biological activity of progesterone itself may be similarly used in the withdrawal test for amenorrhea.

Application of the components, compositions and the methods of this invention for the medical and/or pharmaceutical use which are described in this text can be accomplished by any clinical, medical or pharmaceutical methods or techniques as are presently or prospectively known to those skilled in the art.

The present invention for the first time accomplishes treatment of gonadal-steroid dependent conditions while maintaining production of sufficient endogenous estrogen to mitigate against estrogen depletion side effects. The present invention provides a non-castrating dose of GnRH antagonist which is titered to provide sufficient reduction in endogenous estrogen to inhibit proliferation in endometrial tissue in a menstruating female but is ineffective to substantially stop production of endogenous estrogen. This dose may be effective to provide estrogen in a target range of about 30 to 50 and preferably about 35 to 45 pg/ml in serum which mitigates against menopausal symptoms such as bone loss, hot flushes, etc. This titering of the dose of the GnRH antagonist was accomplished by the first time through the method described above of a progestin withdrawal bleeding test. The lack of bleeding after progestin withdrawal indicates to a physician that sufficient GnRH antagonist has been provided to inhibit production of endogenous estrogen to a level low enough to inhibit proliferation of endometrial tissue. Both circulating estrogen levels and patient response to the residual (basal) ovarian estrogen production will indicate the satisfactory supply of endogenous estrogen.

In order to further illustrate the present invention, a study was carried out as described below. It will be appreciated, however, that this study is illustrative only and is not intended to limit the scope of the invention.

Eleven adult female cynomolgus monkeys having regular and presumably ovulatory menstrual cycles were entered into the study. Body weights were determined monthly. Menstrual bleeding and spotting were recorded daily by visual inspection of external genitalia and insertion of vaginal swabs using a saline moistened cotton-tipped applicator, respectively. Blood samples were collected from femoral vessels and the serum stored for subsequent RIA of estradiol and progesterone. Coefficients of variation for these assays were: 7.4 and 11.1; and 7.0 and 10.9%, respectively, for within and between assays. The GnRH antagonist (GnRHant) used was Nal-Glu: [Ac-D2NAL, 4ClDPhe$^2$, D3Pal$^3$, Arg$^5$, DGlu$^6$(AA), DAla$^{10}$]-GnRH.

In Part I of the study, the object was to perform a brief dose-finding study that indicated residual serum estradiol levels in intact primates previously illustrating regular menstrual cycles. Specifically sought was an approximation of the minimal daily im dose of Nal-Glu sufficient to suppress circulating estradiol levels into the target range: less than 45 pg/ml but more than 35 pg/ml. Beginning on day 2 of the menstrual cycle, Nal-Glu GnRHant, suspended in sesame oil, was administered between 9 and 10 am in doses of 0.1 (n=5) and 0.3 mg/kg (n=6) for 14 days. Femoral blood was obtained daily under ketamine anesthesia. RIA of serum estradiol indicated that whereas the 0.1 mg/kg dose frequently produced circulating estradiol concentrations near the target range (35 to 45 pg/ml), the 0.3 mg/kg dose was too high; that is, serum estradiol levels were predominantly below 30 pg/ml. Accordingly, the Nal-Glu GnRHant dose range was reduced in study Part II.

After a 60 day wash-out interval, the Part II experimental design had two objectives: 1) attempt to titer the GnRHant dose to individual monkeys so that residual ovarian estrogen secretion was often within the target range (estradiol at 35 to 45 pg/ml) in as many of the blood samples as possible; and 2) perform periodic progesterone challenge tests wherein withdrawal bleeding indicates significant estrogen-induced endometrial proliferation (i.e. excessive estrogenic influence) versus amenorrhea (the absence of progesterone withdrawal bleeding) as an indicator that the GnRHant dose and, in turn, the tonic ovarian estrogen production was indicative of a controlled estrogenic milieu.

The design was progressive in that all eleven monkeys initially received Nal-Glu GnRHant at 0.05 mg/kg starting on day 2 of the menstrual cycle and continuing daily until results of the progesterone challenge test and estradiol levels in circulation indicated the need to raise the dose. Concurrently, a pair of progesterone-loaded silastic implants were inserted sc during GnRHant treatment from day 20 and 30, and then removed. If withdrawal menses occurred during the next week, the individual Nal-Glu dose was raised to 0.1 mg/kg daily. On GnRHant treatment day 50, the 10 day progesterone challenge test was repeated for all monkeys. Those primates who were amenorrheic remained on this dose of Nal-Glu; any "bleeders" were to be shifted to a higher dose of GnRHant at 0.2 mg/kg daily through treatment day 90, with the final progesterone challenge test given to all monkeys on days 80 to 90. Again, amenorrhea or withdrawal menses was recorded.

For definition, withdrawal bleeding was scored when blood was on the external genitalia for two or more consecutive days within the week following progesterone withdrawal. Spotting was scored when blood was evident only by coloration of the cotton swab upon insertion into the vagina.

Femoral blood samples were collected every 10 days through the study for RIA of estradiol and progesterone.

The data illustrated in FIG. 1 depict the impact of Nal-Glu GnRHant at two doses on circulating estradiol levels in monkeys over a 14 day treatment interval, beginning on day 2 of the menstrual cycle. Notice that the dose of 0.1 mg/kg im daily led to nearly all mean values within the target zone of 35 to 45 pg/ml of tonic estradiol. While this dose of Nal-Glu appears to be nearly optimal, mean values obscure important individual differences, wherein some data indicate that this GnRHant at 0.1 mg/kg im is too much for some primates whose serum estradiols were predominately <25 pg/ml. Alternatively, other monkeys required a higher GnRHant dose to achieve consistent estradiol levels below 45 pg/ml. Moreover, this dose finding study clearly indicates that 0.3 mg/kg im daily was too much Nal-Glu GnRHant. Indeed, serum estradiol levels were immediately suppressed well below the target zone (even <20 pg/ml) and continued to shift lower still during the 14 day treatment.

From these preliminary findings was devised an individualized progressive GnRHant treatment regimen in order to titer each monkey to an optimal daily dose of Nal-Glu. Beginning at 0.05 mg/kg im, only two primates demonstrated withdrawal amenorrhea after the first progesterone challenge test (see Table 1 below). FIG. 2 shows that their mean serum estradiol levels hovered in or near the target zone. Nine other monkeys manifested frank withdrawal menses. These results confirm the adequacy of the 10 day progesterone treatment via sc silastic implants. Serum progesterone was 6.4±0.6 ng/ml on the final day of the three treatment courses. On day 31, Nal-Glu doses were raised on the other nine females, now receiving 0.1 mg/kg im daily. The second progesterone challenge test resulted in 8 of 9 monkeys achieving withdrawal amenorrhea; one showed overt menstrual bleeding. The two that had remained on 0.05 mg/kg of GnRHant remained amenorrheic upon progesterone withdrawal. FIG. 2 illustrates that increasing the Nal-Glu dose for these 8 monkeys had moderated their mean serum estradiol concentrations to approximately 40 pg/ml.

The lone resistant monkey was changed to a Nal-Glu dose of 0.2 mg/kg im daily (see FIG. 2). The result was excessive estradiol suppression, ultimately to values under 20 pg/ml. The third progesterone challenge test resulted in all eleven monkeys achieving or maintaining amenorrhea, with mean circulating estradiol levels in or near the target zone in all females, except the one given 0.2 mg/kg im daily.

TABLE I

| Week of Progesterone Withdrawal (Days) | Number of Monkeys Per Dose (mg/kg im daily) | | | Amenorrhea Achieved (Monkeys) | Incidence of Spotting (Days) |
|---|---|---|---|---|---|
| | 0.05 | 0.1 | 0.2 | | |
| 31–37 | 11 | — | — | 2/11 | 13 |
| 61–67 | 2 | 8 | — | 10/11 | 12 |
| 91–97 | 2 | 8 | 1 | 11/11 | 0 |

The findings rendered from this primate study demonstrate the utility of titering individualized GnRH ant doses to amenorrhea, while maintaining tonic ovarian estradiol secretion in a milieu suitable for extended therapeutic regimens. For example, estrogen dependency of endometriosis can be controlled by sustaining serum estradiol at levels that do not stimulate endometrial cell proliferation (mitogenesis) either in utero or ectopically. At the same time, the reduction of estradiol levels in circulation is quite modest and can be titered to near or slightly below 40 pg/ml by individual adjustment of the GnRHant dose, depending on whether a progesterone challenge test results in withdrawal amenorrhea. This regimen is conducive to achieving amenorrhea with the lowest effective dose of GnRHant, while providing modest levels of endogenous estrogen and averting frank hypoestrogenism. Accordingly, extended treatment intervals can be justified; indeed, titering of the GnRHant dose alone allows a number of years of therapy, instead of a 6-month limitation due to severe estrogen deficiency, as occurs using GnRH agonist as a nearly all or none inhibitor.

The data clearly point to the need for a highly individualized GnRHant regimen. This new therapeutic approach is more favorable than GnRH agonist alone or GnRH agonist plus "add back" HRT: first because it avoids the complexity and cost of overlapping to two treatment regimens; secondly, because the potential mal-effects of exogenous estrogen-progestin regimens on metabolism are averted. Notice that by titering each individual primate to amenorrhea, endometrial mitogenic quiescence negates the need for progestin therapy to counter excessive estrogen only exposure, and, in turn, associated risks of endometrial hyperplasia or endometrial carcinoma are not confronted. It follows that a series of gynecologic disorders that are substantially estrogen-dependent may be managed therapeutically by titering patients to the lowest dose of GnRHant needed to reach the individual threshold for amenorrhea. This regimen conserves a considerable degree of endogenous ovarian estrogen production which can sustain bone density and cardiovascular health, as well as moderating hot flushes. Accordingly, titering individualized GnRHant doses to amenorrhea, with maintenance of tonic estradiol in circulation may allow long-term courses of treatment which avoid sacrificing either therapeutic efficacy of a controlled estrogenic milieu or the positive dimensions of estrogen action for overall female health maintenance.

Various changes and modifications can be made in the present invention without departing from the spirit and scope thereof. The various embodiments which have been described and illustrated above where intended to be representative and not limiting.

What is claimed is:

1. A regimen for the therapeutic management of a gonadal-steroid dependent condition in a mammal by reducing the estrogen supply thereof by means of administration of a GnRH antagonist in an amount effective to inhibit proliferation of endometrial tissue without substantially stopping the production of endogenous estrogen.

2. The regimen of claim 1 wherein the mammal is a menstruating female.

3. The regimen of claim 2 wherein the amount is determined by administering the GnRH antagonist to the female at a given dosage level and conducting a progesterone challenge test on that female.

4. The regimen of claim 3 wherein the dosage of GnRH antagonist administered is changed after the challenge test and an additional progesterone challenge test is conducted on the female.

5. The regimen of claim 4 in which the sequence of dosage change and additional challenge test is conducted more than once.

6. The regimen of claim 1 wherein the dose is administered a plurality of times in a cumulative amount effective to inhibit proliferation of endometrial tissue without being a sufficient amount to induce a castrate level of endogenous estrogen.

7. The regimen of claim 6 wherein the amount effective to inhibit proliferation of endometrial tissue is effective to prevent withdrawal bleeding in response to a progesterone challenge test.

8. A method of reducing the proliferation of endometrial tissue in a menstruating female without inducing a castrate level of endogenous estrogen comprising the steps of administering a regimen of GnRH antagonist in an amount and on a predetermined schedule which is effective to inhibit proliferation of endometrial tissue in the menstruating female but is ineffective to substantially stop production of endogenous estrogen.

9. The method of claim 8 wherein the GnRH antagonist is provided in an amount which is effective to provide an average 24 hour serum estradiol from about 30 to 50 pg/ml.

10. The method of claim 9 wherein the GnRH antagonist is provided in an amount which is effective to provide an average 24 hour serum estradiol from about 30 to 45 pg/ml.

11. A method of reducing the proliferation of endometrial tissue in a menstruating female without inducing a castrate level of endogenous estrogen comprising the steps of administering a dose of GnRH antagonist in an amount which is effective to inhibit proliferation of endometrial tissue in the menstruating female but is ineffective to substantially stop production of endogenous estrogen.

12. The method of claim 11 wherein the GnRH antagonist is provided in an amount which is effective to provide an average 24 hour serum estradiol from about 30 to 50 pg/ml.

13. The method of claim 12 wherein the serum estradiol level is about 35 to 45 pg/ml.

14. A method of reducing gonadal-steroid dependent conditions in a menstruating female without inducing a castrate level of endogenous estrogen comprising the steps of administering a regimen of GnRH antagonist in an amount and on a predetermined schedule which is effective to inhibit proliferation of endometrial tissue in the menstruating female but is ineffective to substantially stop production of endogenous estrogen.

15. The method of claim 14 wherein the GnRH antagonist is provided in an amount which is effective to provide an average 24 hour serum estradiol from about 30 to 50 pg/ml.

16. The method of claim 15 wherein the serum estradiol level is about 35 to 45 pg/ml.

17. A method of reducing gonadal-steroid dependent conditions in a menstruating female without inducing a castrate level of endogenous estrogen comprising the Steps of administering a dose of GnRH antagonist in an amount which is effective to inhibit proliferation of endometrial tissue in a menstruating female but is ineffective to substantially stop production of endogenous estrogen.

18. The method of claim 17 wherein the GnRH antagonist is provided in an amount which is effective to provide an average 24 hour serum estradiol from about 30 to 50 pg/ml.

19. The method of claim 18 wherein the serum estradiol level is from about 35 to 45 pg/ml.

20. A method of determining whether a reduced estrogenic milieu in an individual mammal is such that the concentration of estradiol has been suppressed to an optimized level appropriate to the therapeutic management of gonadal-steroid dependent condition in that individual by administering a GnRH antagonist to the individual at a given dosage level which comprises titering the antagonist dosage.

21. The method of claim 20 wherein the titering comprises conducting a progesterone challenge test on that individual, whereby amenorrhea indicates adequate suppression of production of endogenous estrogen.

22. The method of claim 21 wherein the dosage of GnRH antagonist administered is changed after the challenge test and an additional progesterone challenge test is conducted on the individual.

23. The method of claim 21 wherein the dosage level is changed by increasing the dosage.

24. The method of claim 23 wherein the level is changed by decreasing the dosage.

25. The method of claim 22 in which the sequence of dosage change and additional challenge test is conducted more than once.

26. The method of claim 20 wherein the gonadal-steroid dependent condition is endometriosis.

27. The method of claim 20 wherein the gonadal-steroid dependent condition is leiomyomata.

28. The regimen of claim 1 wherein the dose is administered a plurality of times in a cumulative amount effective to inhibit proliferation of endometrial tissue without being a sufficient amount to substantially accelerate bone loss associated with protracted estrogen deprivation.

29. The regimen of claim 1 wherein the dose is administered a plurality of times in a cumulative amount effective to inhibit proliferation of endometrial tissue without being a sufficient amount to enhance cardiovascular risk factors associated with protracted estrogen deprivation.

30. The regimen of claim 1 wherein the dose is administered a plurality of times in a cumulative amount effective to inhibit proliferation of endometrial tissue without being a sufficient amount to induce hot flashes associated with protracted estrogen deprivation.

* * * * *

UNITED STATES PATENT AND TRADEMARK OFFICE
CERTIFICATE OF CORRECTION

PATENT NO. : 5,658,884
DATED : August 19, 1997
INVENTOR(S) : Gary D. HODGEN, et al.

It is certified that error appears in the above-indentified patent and that said Letters Patent is hereby corrected as shown below:

On the title page, item: under "[75] Inventor:" read --Gary D. HODGEN, Norfolk, Virginia and Audrey Phillips, Somerville, New Jersey--

Signed and Sealed this

Fourteenth Day of July, 1998

Attest:

BRUCE LEHMAN

*Attesting Officer*  *Commissioner of Patents and Trademarks*